(12) United States Patent
Lassalas et al.

(10) Patent No.: US 11,191,606 B2
(45) Date of Patent: Dec. 7, 2021

(54) ILLUMINATING OPHTHALMIC ENDOPROBE

(71) Applicant: Alcon Inc., Fribourg (CH)

(72) Inventors: Bruno Lassalas, Foothill Ranch, CA (US); Chenguang Diao, Irvine, CA (US); Alireza Mirsepassi, Irvine, CA (US); Kambiz Parto, Laguna Niguel, CA (US); Mark Harrison Farley, Laguna Hills, CA (US)

(73) Assignee: Alcon Inc., Rue Louis-d'affry (CH)

( * ) Notice: Subject to any disclaimer, the term of this patent is extended or adjusted under 35 U.S.C. 154(b) by 169 days.

(21) Appl. No.: 16/378,886

(22) Filed: Apr. 9, 2019

(65) Prior Publication Data

US 2019/0314111 A1 Oct. 17, 2019

Related U.S. Application Data

(60) Provisional application No. 62/656,238, filed on Apr. 11, 2018.

(51) Int. Cl.
| | | |
|---|---|---|
| *A61B 90/30* | (2016.01) | |
| *A61F 9/008* | (2006.01) | |
| *A61B 1/00* | (2006.01) | |
| *A61B 1/06* | (2006.01) | |
| *A61B 3/00* | (2006.01) | |
| *A61B 5/00* | (2006.01) | |

(52) U.S. Cl.
CPC .............. *A61B 90/30* (2016.02); *A61F 9/008* (2013.01); *A61B 1/00172* (2013.01); *A61B 1/0661* (2013.01); *A61B 3/0008* (2013.01); *A61B 5/0059* (2013.01); *A61B 2090/306* (2016.02)

(58) Field of Classification Search
CPC . A61B 90/30; A61B 2090/306; A61B 1/0661; A61B 3/0008
See application file for complete search history.

(56) References Cited

U.S. PATENT DOCUMENTS

| | | |
|---|---|---|
| 7,618,177 B2 | 11/2009 | Cazzini |
| 8,398,240 B2 | 3/2013 | Smith |
| 8,480,233 B2 | 7/2013 | Smith |
| 8,480,279 B2 | 7/2013 | Papac et al. |

(Continued)

FOREIGN PATENT DOCUMENTS

| | | | |
|---|---|---|---|
| WO | WO-2016166642 A1 * | 10/2016 | ............ A61M 25/00 |
| WO | WO2016166642 A1 | 10/2016 | |

*Primary Examiner* — Julianna N Harvey (57) ABSTRACT

In certain embodiments, an illuminating endoprobe system includes one or more light sources, a housing, a vitreous visualization fiber, and a general illumination fiber. The light sources generate a visualization light and an illumination light. The housing receives the visualization and illumination light, and has a probe tip with a probe axis. The vitreous visualization fiber transmits the visualization light through the probe tip. The visualization light has a visualization axis and a visualization beam angle at the probe tip. The general illumination fiber transmits the illumination light through the probe tip. The illumination light has an illumination axis and an illumination beam angle at the probe tip. The illumination beam angle is greater than the visualization beam angle, and the illumination axis is at an offset angle relative to the visualization axis, where the offset angle greater than 5 degrees.

18 Claims, 7 Drawing Sheets

(56) References Cited

U.S. PATENT DOCUMENTS

| | | |
|---|---|---|
| 8,485,972 B2 | 7/2013 | Papac et al. |
| 8,900,139 B2 | 12/2014 | Yadlowsky |
| 8,968,347 B2 | 3/2015 | McCollam |
| 9,510,848 B2 | 12/2016 | Auld |
| 10,016,248 B2 | 7/2018 | Mirsepassi |
| 10,307,290 B2 | 6/2019 | Kern |
| 10,478,266 B2 | 11/2019 | Mirsepassi |
| 10,537,401 B2 | 1/2020 | Dos Santos |
| 2008/0246919 A1* | 10/2008 | Smith .................. A61B 3/0008 351/213 |
| 2012/0041461 A1 | 2/2012 | McCollam |
| 2013/0079598 A1 | 3/2013 | Auld et al. |
| 2016/0302878 A1 | 10/2016 | Kern |
| 2017/0280989 A1 | 10/2017 | Heeren |
| 2018/0055596 A1 | 3/2018 | Johnson |
| 2018/0133057 A1 | 5/2018 | Diao |
| 2018/0140179 A1 | 5/2018 | Labelle |
| 2018/0168861 A1 | 6/2018 | Mirsepassi |
| 2018/0243137 A1 | 8/2018 | Diao |
| 2019/0142544 A1 | 5/2019 | Horn |
| 2019/0209372 A1 | 7/2019 | Farley |
| 2019/0282322 A1 | 9/2019 | Mirsepassi |

* cited by examiner

ILLUMINATING OPHTHALMIC ENDOPROBE

PRIORITY CLAIM

This application claims the benefit of priority of U.S. Provisional Patent Application Ser. No. 62/656,238 titled "Illuminating Ophthalmic Endoprobe," filed on Apr. 11, 2018, whose inventors are Bruno Lassalas, Chenguang Diao, Alireza Mirsepassi, Kambiz Parto, and Mark Harrison Farley, which is hereby incorporated by reference in its entirety as though fully and completely set forth herein.

TECHNICAL FIELD

The present disclosure relates generally to ophthalmic surgical devices, and more specifically to an illuminating ophthalmic endoprobe.

BACKGROUND

Ophthalmic surgery is performed on the eye to improve vision. Ophthalmic surgery can, e.g., repair retinal defects, remove cataracts, or shape the cornea. During ophthalmic surgery, the surgeon may want to see the vitreous of the eye, e.g., to remove it. The vitreous, which is a gel-like substance located between the lens and retina, contains photoreceptors sensitive to light, and is thus transparent and colorless to allow light to pass largely unimpeded to the retina. Although these properties are excellent for the normal functions of the eye, they make it difficult to see the vitreous to be removed during surgery.

BRIEF SUMMARY

In certain embodiments, an illuminating endoprobe system includes one or more light sources, a housing, a vitreous visualization fiber, and a general illumination fiber. The one or more light sources generate a visualization light and an illumination light. The housing receives the visualization light and the illumination light, and has a probe tip with a probe axis. The vitreous visualization fiber is disposed within the probe tip and has a distal end. The vitreous visualization fiber transmits the visualization light through the probe tip, where the visualization light has a visualization axis and a visualization beam angle at the probe tip. The general illumination fiber is disposed within the probe tip and has a distal end. The general illumination fiber transmits the illumination light through the probe tip, where the illumination light has an illumination axis and an illumination beam angle at the probe tip. The illumination beam angle is greater than the visualization beam angle, and the illumination axis is at an offset angle relative to the visualization axis, the offset angle greater than 5 degrees.

In certain embodiments, a method for providing illumination and visualization includes generating a visualization light and an illumination light. The visualization light and the illumination light is received at a housing that has a probe tip with a probe axis. The visualization light is transmitted via a vitreous visualization fiber through the probe tip. The vitreous visualization fiber is disposed within the probe tip and has a distal end. The visualization light has a visualization axis and a visualization beam angle at the probe tip. The illumination light is transmitted via a general illumination fiber through the probe tip. The general illumination fiber is disposed within the probe tip and has a distal end. The illumination light has an illumination axis and an illumination beam angle at the probe tip. The illumination beam angle is greater than the visualization beam angle, and the illumination axis is at an offset angle relative to the visualization axis, the offset angle greater than 5 degrees.

Certain embodiments may have other features, including: (1) the distal end of the vitreous visualization fiber ramped relative to the probe axis, the ramped distal end transmitting the visualization light with the visualization axis that is not parallel to the probe axis; (2) the distal end of the vitreous visualization fiber having an angled surface, the angled surface transmitting the visualization light with the visualization axis that is not parallel to the probe axis to yield the offset angle with the illumination axis; (3) the distal end of the general illumination fiber having an angled surface, the angled surface transmitting the illumination light with the illumination axis that is not parallel to the probe axis to yield the offset angle with the visualization axis; (4) the distal end of the vitreous visualization fiber having a first angled surface that transmits the visualization light with the visualization axis, the distal end of the general illumination fiber having a second angled surface that transmits the illumination light with the illumination axis, the illumination axis and the visualization axis yielding the offset angle; (5) the one or more light sources comprising: a visualization source configured to generate the visualization light, and an illumination source configured to generate the illumination light; (6) the one or more light sources comprising: a visualization source configured to generate the visualization light, and an illumination source configured to generate the illumination light, a luminous flux of the visualization source greater than a luminous flux of the illumination source; (7) the offset angle less than 30 degrees; and (8) the visualization light and the illumination light yielding non-concentric illumination patterns.

BRIEF DESCRIPTION OF THE DRAWINGS

Embodiments of the present disclosure are described by way of example in greater detail with reference to the attached figures, in which:

FIGS. 5A through 6B illustrate examples of visualization fibers and illumination fibers that yield non-concentric patterns:

DESCRIPTION OF EXAMPLE EMBODIMENTS

Referring now to the description and drawings, example embodiments of the disclosed apparatuses, systems, and methods are shown in detail. As apparent to a person of ordinary skill in the field, the disclosed embodiments are exemplary and not exhaustive of all possible embodiments.

The present disclosure describes embodiments of an endoprobe for visualizing the vitreous during ophthalmic surgery. The endoprobe may be used during vitreoretinal surgery, e.g., during a vitrectomy, in which vitreous is removed from the eye. The endoprobe improves the ability to see the vitreous by including a vitreous illuminator along with a general illuminator, where the vitreous illuminator provides visualization light at an offset angle relative to illumination light provided by the general illuminator. The offset of the vitreous illumination light relative to the general illumination light improves access to peripheral vitreous visualization. It also improves the vitreous visualization by shifting the general illumination light reflected back from the retina out of surgeon's view. Moreover, the vitreous illuminator provides the visualization light with a more focused beam angle than that of the illumination light. In addition, the visualization light may have other properties that facilitate visualizing the vitreous, such as a particular color or greater luminous flux than that of the illumination light. Overall, the endoprobe may allow the normally clear vitreous to have a smoky appearance, similar to normally invisible dust particles in a laser beam.

Figure 1:
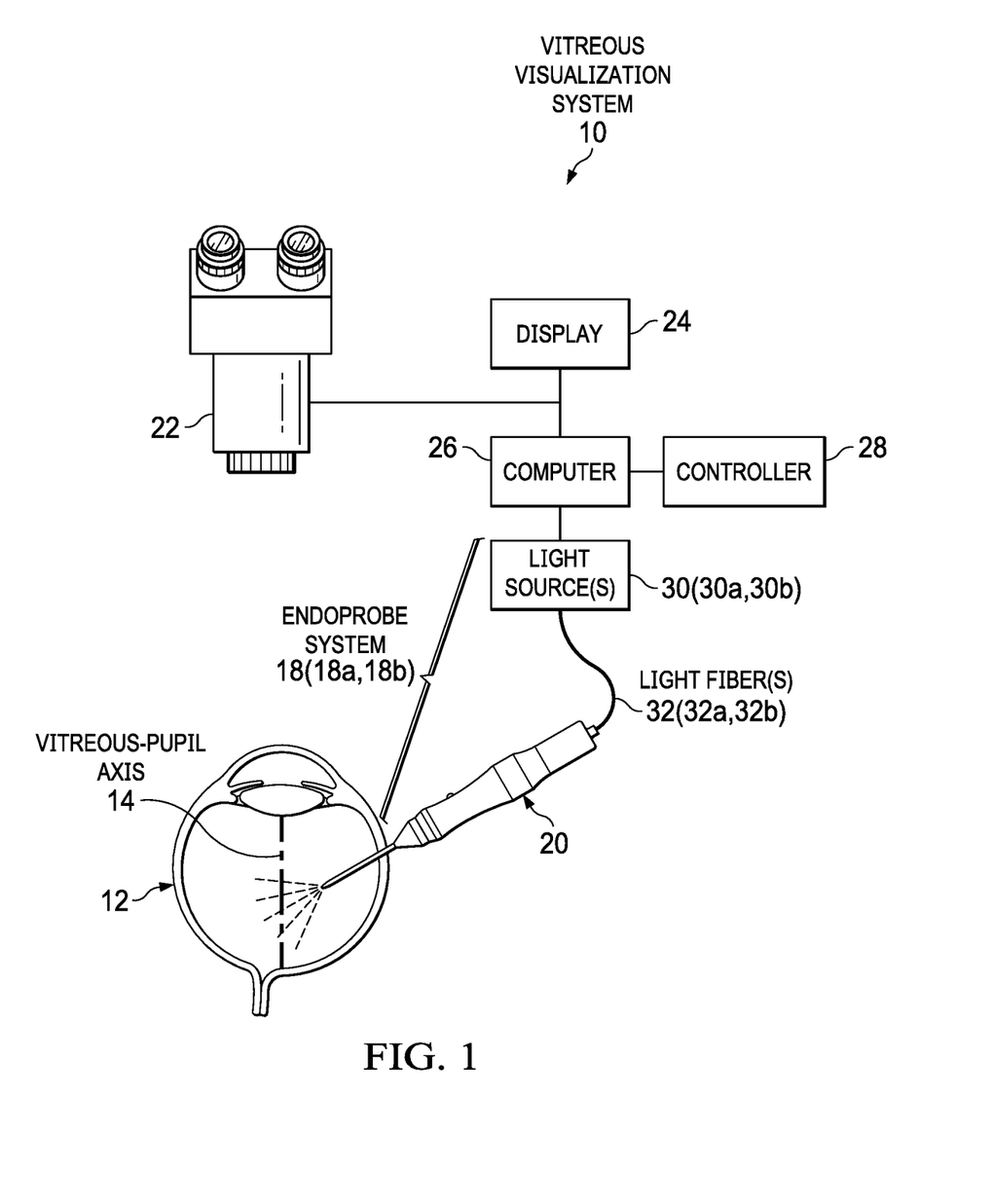
FIG. 1 illustrates an embodiment of a vitreous visualization system for visualizing the vitreous of an eye.

FIG. 1 illustrates an embodiment of a vitreous visualization system 10 for visualizing the vitreous of an eye 12. In the illustrated embodiment, system 10 includes an endoprobe system 18, a microscope 22, a display 24, a computer 26, and a controller 28. Endoprobe system 18 includes an endoprobe 20, light sources 30 (visualization 30a and/or illumination 30b sources), and light fibers 32 (visualization 32a and/or illumination 32b fibers). Endoprobe system 18 includes a vitreous illuminator 18a with visualization light source 30a and visualization fiber 32a, and a general illuminator 18b with illumination light source 30b and illumination fiber 32b.

In an example of operation, light sources 30 generate light, which is received by fibers 32, either directly or via other fibers and/or connectors. Visualization fiber 32a transmits light ("visualization light") from visualization light source 30a, and illumination fiber 32b transmits light ("illumination light") from illumination light source 30b. Endoprobe 20 directs the light into eye 12 to visualize the vitreous of eye 12 and illuminate the interior of eye 12, which has a vitreous-pupil axis 14. Microscope 22 and/or display 24 may provide images of the vitreous and interior. Computer 20 controls the operation of system 10, and a user may control the use of system 10 using controller 28.

In certain embodiments, a light source 30 may be any suitable light source (e.g., a supercontinuum laser, a white light source, or any other suitable light source) that generates light. A fiber 32 includes any material that substantially transmits light, such as an optical fiber. In certain embodiments, visualization fiber 32a may have a smaller diameter than that of illumination fiber 32b. For example, visualization fiber 32a may have a diameter in the range of 30 to 50, 50 to 80, 80 to 100, or 100 to 150 microns, and illumination fiber 32b may have a diameter in the range of 29 to 27 or 27 to 25 gauge.

Endoprobe 20 enters eye 12 and allows system 10 to illuminate the interior of eye 12 with visualization and illumination light. Endoprobe 20 is described in more detail with reference to FIGS. 3A and 3B.

Figure 2:
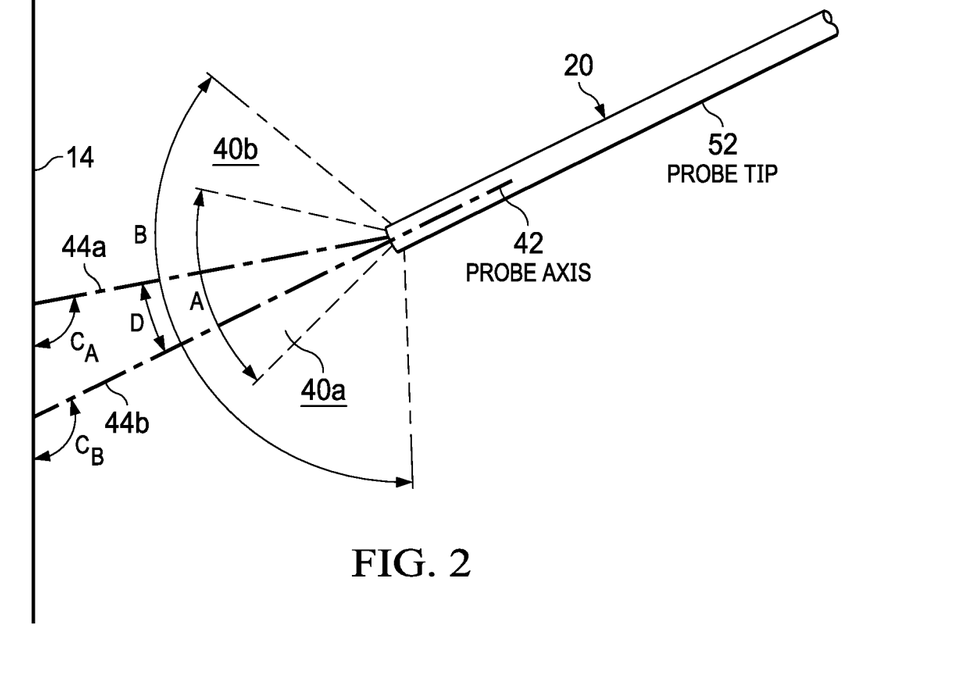
FIG. 2 illustrates visualization light and illumination light exiting the endoprobe of the system of FIG. 1.

FIG. 2 illustrates visualization light 40a and illumination light 40b exiting endoprobe 20 of system 10. In the example, endoprobe 20 has a probe tip 52 with a probe axis 42. Visualization light 40a exits probe tip 52 with a visualization beam angle A and a visualization axis 44a, and illumination light 40b exits with an illumination beam angle B and an illumination axis 44b. Axes 44 of light 40 form angles C with vitreous-pupil axis 14. Visualization axis 44a forms an angle CA with vitreous-pupil axis 14, and illumination axis 44b forms an angle CB with axis 14. Visualization axis 44a and illumination axis 44b form an offset angle D, where offset angle may be in the range of 5 to 10, 10 to 20, 20 to 30, or greater than 30 degrees. Embodiments of fibers 32 that yield offset angle D are described in more detail with reference to FIGS. 5A to 7B.

Referring back to FIG. 1, computer 26 controls the operation of system 10. For example, computer 26 may control whether visualization source 30a or illumination source 30b or both provide light, and the luminous flux or wavelengths of the light. Computer 26 may vary the on/off status, luminous flux, and/or wavelengths of light to improve visibility of the vitreous or to avoid phototoxicity or other negative effects. Computer 26 may also perform other functions. For example, computer 26 may track the total amount of light output by vitreous illuminator 18a or general illuminator 18b or both, and may provide this information to the surgeon or automatically adjust light output to not exceed preset thresholds for total light output.

Surgical microscope 22 may allow the user to view an optical or digital image of eye 12. Display 24 may be a screen or head up display that can display an image of eye 12. In certain embodiments, surgical microscope 22 and/or display may display other information in addition to an image of eye 12, such as warnings, graphs, or augmented reality information.

In addition to providing the visualization and illumination light with offset angle D, system 10 may use other techniques to visualize the vitreous. The visibility of the vitreous can depend on the following: (1) the luminous flux of the visualization light; (2) the color of the visualization light; (3) visualization beam angle A; (4) the angle between visualization axis 44a and vitreous-pupil axis 14; and (5) other features of the visualization light.

(1) Luminous Flux.

The visibility of the vitreous may be improved by increasing the ratio of brightness of the vitreous to brightness of retina. This ratio can be increased by increasing the ratio of the luminous flux of the visualization light to that of the illumination light, which depends mainly on the relative luminous flux of visualization source 30a and of illumination source 30b. The luminous flux of the visualization light (at probe tip 52) may be in the range of 0.5 to 1, 1 to 2, 2 to 5, or 5 to 10 lumens, and may be least 2, 5, 10, or 20 times higher than the luminous flux of illumination source 30b.

(2) Color.

The visualization light may be white or any other suitable color. For example, yellow, green, and blue light render the vitreous readily visible against the retina, and their shorter wavelengths are scattered well by the vitreous. Colors that are more similar to the retina or at longer wavelengths that are not scattered well by the vitreous, such as red or orange, may still be used. Visibility of the vitreous may be improved by using different colors for the visualization and illumination light. For example, the illumination light may be white, and the visualization light may be green. However, it should be noted that shorter wavelengths of light may be more likely to cause accidental damage to the eye, such that very short wavelengths may be avoided.

(3) Beam Angle.

In certain embodiments, illumination beam angle B is greater than visualization beam angle A. In these embodiments, visualization beam angle A may be in the range of less than 20, 20 to 25, 25 to 30, or 30 to 45 degrees. The smaller beam angle may be achieved by, e.g., using a low NA fiber for visualization fiber 32a. Illumination beam angle B may be greater than angle A by a difference in the range of 10 to 25, 25 to 50, 50 to 75, or great than 75.

(4) Angle Relative to Eye Axis.

The angle C between axis 44 of light 40 and vitreous-pupil axis 14 affects the visibility of the vitreous. If the angle C between axis 44 of light 40 and vitreous-pupil axis 14 is smaller, then light is directed more towards the exterior of eye 12 and less towards the retina, which reduces the illumination of the retina, thereby decreasing the ratio of brightness of the vitreous to brightness of the retina. Moreover, endoprobe 20 may be positioned such that angle CB for illumination light 40b is less than angle CA for visualization light 40a, reducing illumination of the retina even more. However, endoprobe 20 may be positioned in any suitable manner to allow for optimal illumination and visualization.

(5) Other Features.

Vitreous illuminator 18a may provide light in a flashing or pulsing pattern to further enhance visibility of the vitreous, particularly when general illuminator 18b provides white light.

Figure 3A:
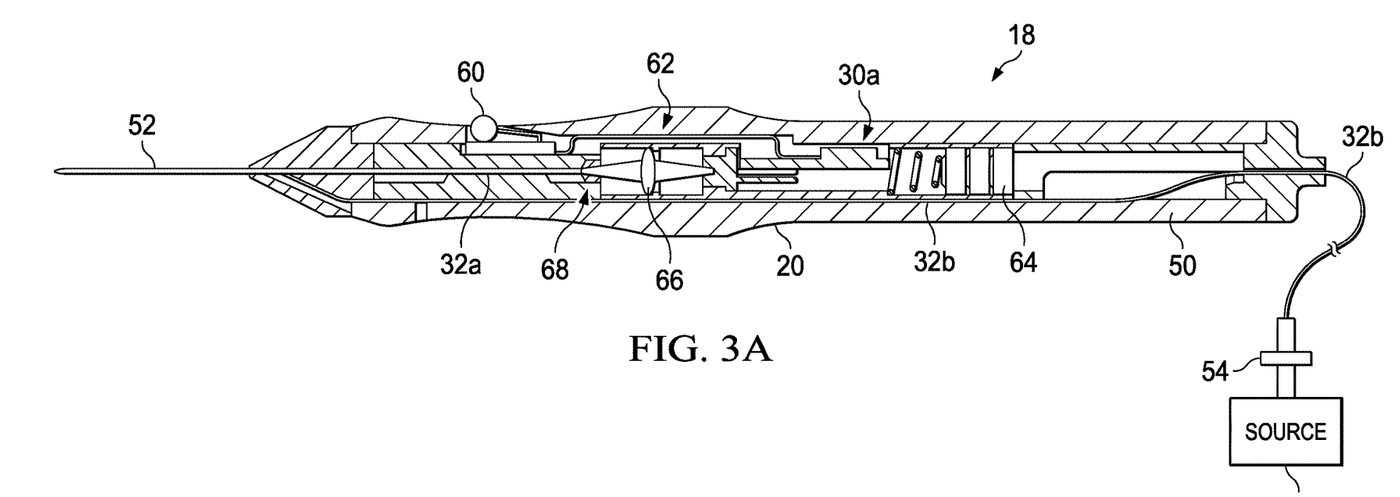
FIGS. 3A and 3B illustrate an example of endoprobe system that may be used with the system of FIG. 1.
Figure 3B:
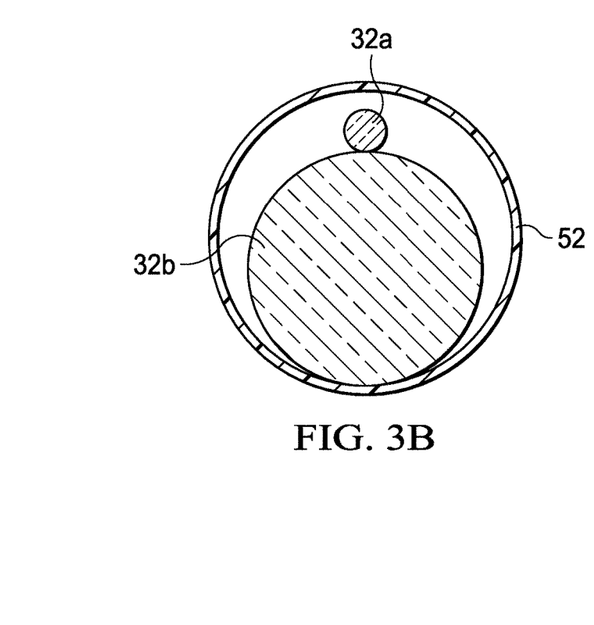

Modifications may be made to the illustrated system 10. As an example, although the illustrated system 10 has light sources 30 separated from endoprobe 20, one or more sources 30 can be disposed inside of endoprobe 20, e.g., visualization source 30a or illumination source 30b or both may be disposed inside of endoprobe 20. As another example, although the illustrated system 10 is described as having separate visualization 30a and illumination 30b sources and separate visualization 32a and illumination 32b fibers, a combined light source 30 and a partially combined fiber 32 with a splitter may be used. Visualization light may be supplied to one optical fiber (e.g., the core optical fiber of a multi-core optical fiber), while illumination light may be supplied to another optical fiber (e.g., as an exterior optical fiber of a multi-core optical fiber). FIGS. 3A and 3B illustrate an example of endoprobe system 18 that may be used with vitreous visualization system 10. Endoprobe system 18 includes endoprobe 20 that has a housing 50 with a probe tip. Visualization source 30a, fibers 32a and 32b, a laser controller 60, a circuit 62, a battery 64, a collimator 66, and a condenser 68 are disposed within housing 50. Visualization source 30a may be a laser that generates visualization light. The light may pass through optical components, e.g., collimator 66 and condenser 68, before entering visualization fiber 30a. Laser controller 60 may be accessible from outside of housing 50 to allow a user to control visualization source 30a, e.g., turn the light on or off and/or control the luminous flux of the light. Controller 60 may be electrically connected to laser visualization source 30a via circuit 62. Battery 64 provides power to visualization source 30a.

Illumination fiber 32b may be coupled to illumination source 30b with connector 54. Probe tip 52 may include a thin tube, such as a metal tube, that houses visualization fiber 30a and illumination fiber 30b. Probe tip 52 may be small to avoid trauma to the eye 12, e.g., may have a diameter in the range of 20 to 23, 23 to 25, or less than 25 gauge. FIG. 3B diagram shows a cross-section of fibers 32a and 32b disposed within probe tip 52.

Although the example endoprobe system 18 shows visualization source 30a located within housing 50 and illumination source 30b located outside of housing 50, illumination source 30b may be located inside and visualization source 30a outside, or both may be located inside or both outside. In these embodiments, housing 50 may be referred to a receiving illumination and visualization light, regardless of whether sources 30a and 30b are located inside or outside of housing 50.

FIGS. 4A through 6B illustrate examples of visualization fiber 32a and illumination fiber 32b emitting visualization 40a and illumination 40b light, respectively, with axes 44a and 44b, respectively. Each A diagram shows a longitudinal view of the distal ends of fibers 32a and 32b at the distal end 47 of probe tip 52. Each B diagram shows the generally circular or oval patterns 48 formed by light 40a and 40b. Visualization light forms visualization pattern 48a and illumination light forms illumination pattern 48b at a plane substantially normal to probe axis 42. In the examples, the beam angle of visualization light 40a is smaller than that of illumination light 40b, so pattern 48a is smaller than pattern 48b. At an axial distance of 10 mm, the circular area produced by illumination light 40b may have a diameter two to three times larger than that of visualization light 40a.

Figure 4A:
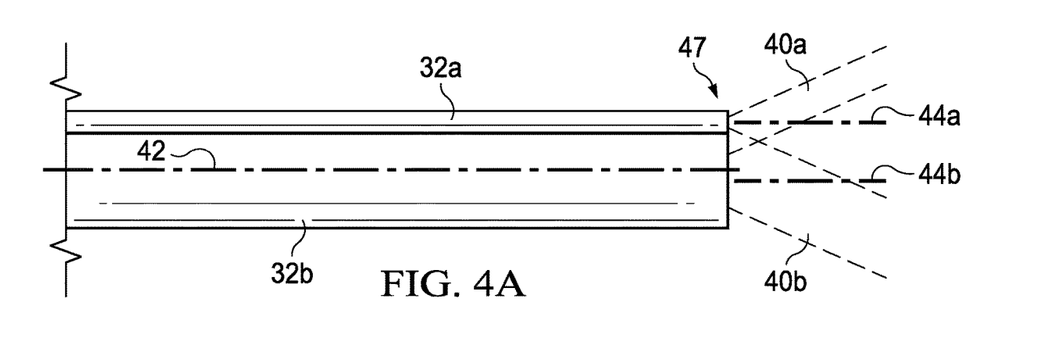
FIGS. 4A and 4B illustrate an example of a visualization fiber and an illumination fiber that yield concentric patterns.
Figure 4B:
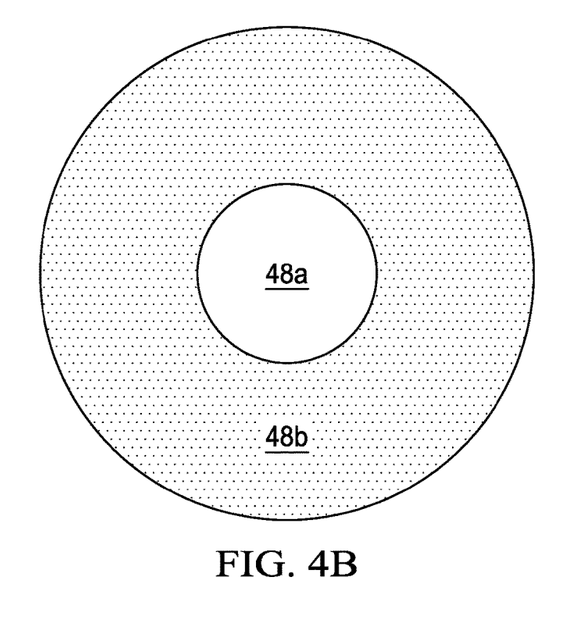

FIGS. 4A and 4B illustrate an example of visualization fiber 32a and illumination fiber 32b that yield concentric illumination patterns 48a and 48b. In the example, axes 44a and 44b are substantially parallel to probe axis 42, and angle D between the respective axes 44a and 44b is substantially zero.

FIGS. 5A through 6B illustrate examples of visualization fiber 32a and illumination fiber 32b that yield non-concentric illumination patterns 48a and 48b. In the examples, axis 44a or axis 44b or both are not parallel to probe axis 42, so angle D between axes 44a and 44b is an offset angle that is greater than zero. The offset of the vitreous illumination light relative to the general illumination light improves access to peripheral vitreous visualization. It also improves the vitreous visualization by shifting the general illumination light reflected back from the retina out of surgeon's view.

Offset angle D yields non-concentric patterns 48a and 48b, where visualization pattern 48a is between the center and circumference of pattern 48b. In certain examples, pattern 48a may be closer to the circumference of pattern 48b and may be at or even overlap the circumference. This arrangement of patterns 48a and 48b may allow for improved visualization of the vitreous at the edge of the illumination. Moreover, the non-concentric patterns 48a and 48b allow endoscope 20 to direct visualization 40a and illumination 40b light to different areas. For example, visualization light 40a may be directed to a desired area of the vitreous, and illumination light 40b may be directed away from the retina to reduce brightness of the retina and improve visualization of the vitreous.

Figure 5A:
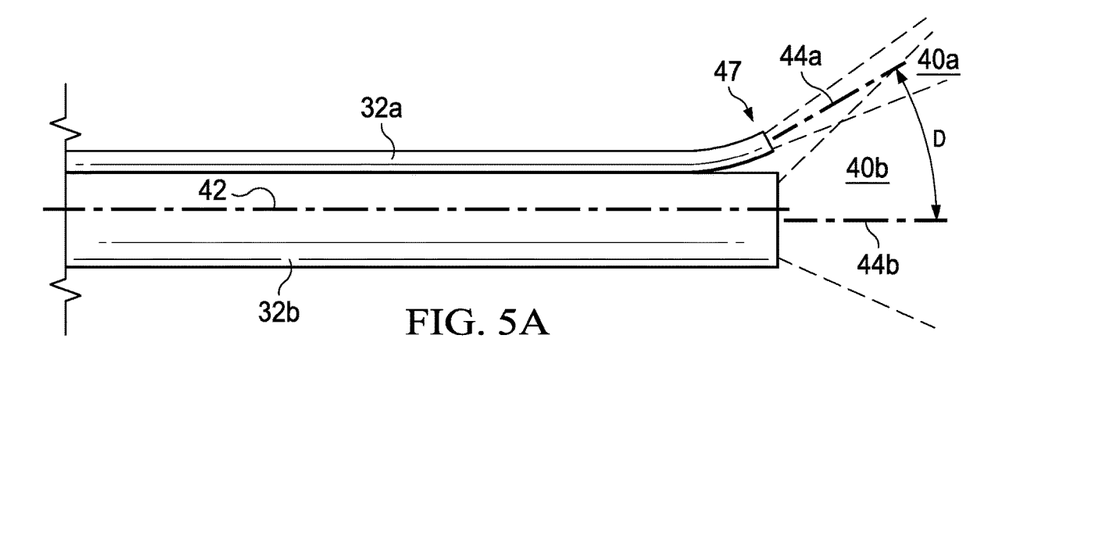
FIGS. 5A and 5B illustrate an example where the distal end of the visualization fiber is ramped relative to the probe axis.
Figure 5B:
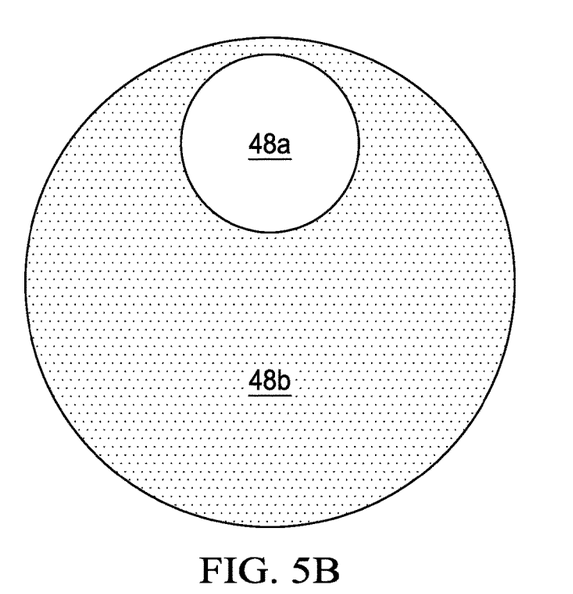

FIGS. 5A and 5B illustrate an example where the distal end of visualization fiber 32a is ramped relative to probe axis 42 and relative to the distal end of illumination fiber 32b. Visualization fiber 32a is ramped, i.e., curved at the distal end. The ramped end yields visualization light with axis 44a that is not parallel to probe axis 42 and results in the desired offset angle D with axis 44b. Any suitable curvature may be used. Generally, the curvature is small, e.g., curvature $\kappa=1/R$ may be in a range of $1/5$ to $1/10$, $1/10$ to $1/25$, or $1/25$ or less, where R represents the radius of a circle in centimeters (cm).

Figure 6A:
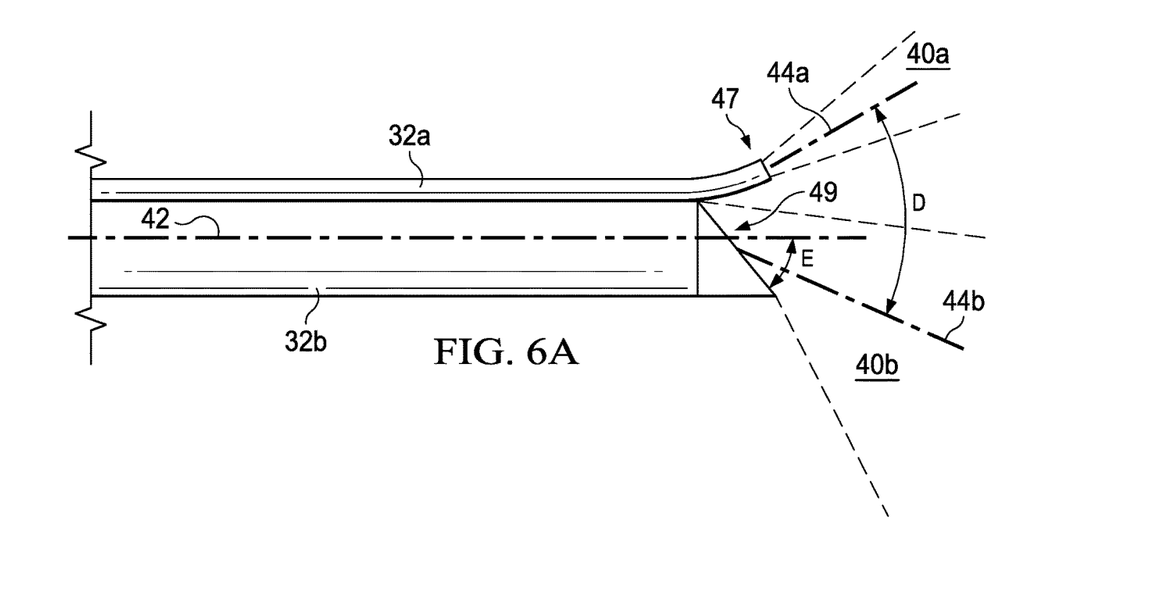
FIGS. 6A and 6B illustrate an example where the distal end of the visualization fiber is ramped and the distal end of the illumination fiber has an angled surface.
Figure 6B:
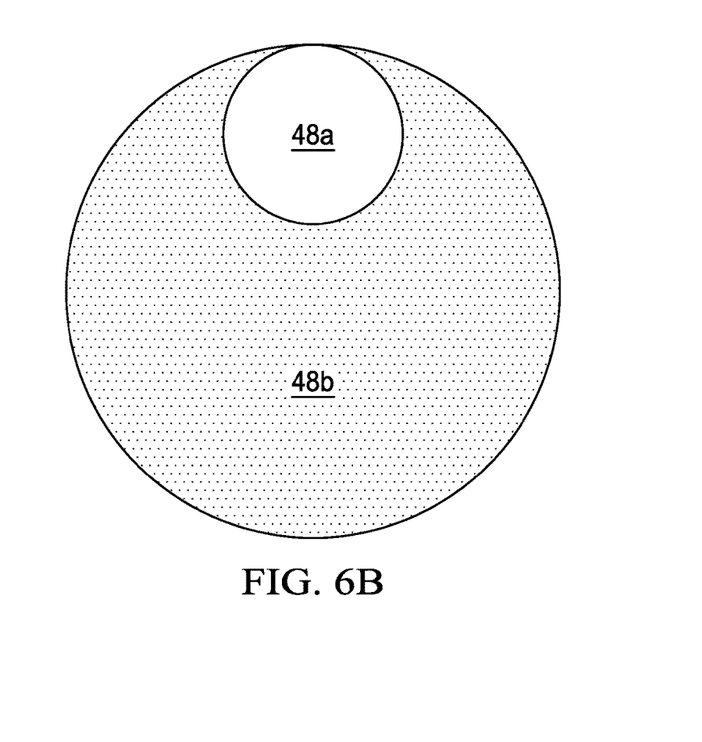

FIGS. 6A and 6B illustrate an example where the distal end of visualization fiber 32a is ramped and the distal end of illumination fiber 32b has an angled surface 49. Angled surface 49 has an angle E relative to probe axis 42. Angle E may be any angle suitable to yield illumination light 40b with axis 44b that results in the desired offset angle D with axis 44a. For example, angle E may be in a range of 10 to 25, 25 to 50, or 50 to 75 degrees.

Figure 7A:
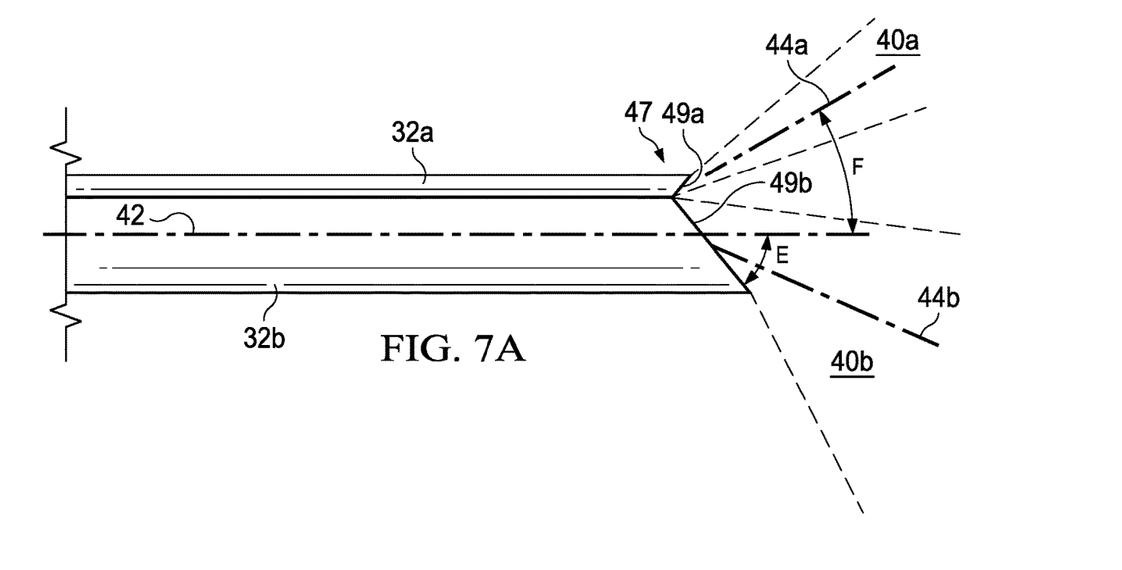
FIGS. 7A and 7B illustrate an example where the distal end of the visualization fiber has an angled surface and the distal end of the illumination fiber also has an angled surface.
Figure 7B:
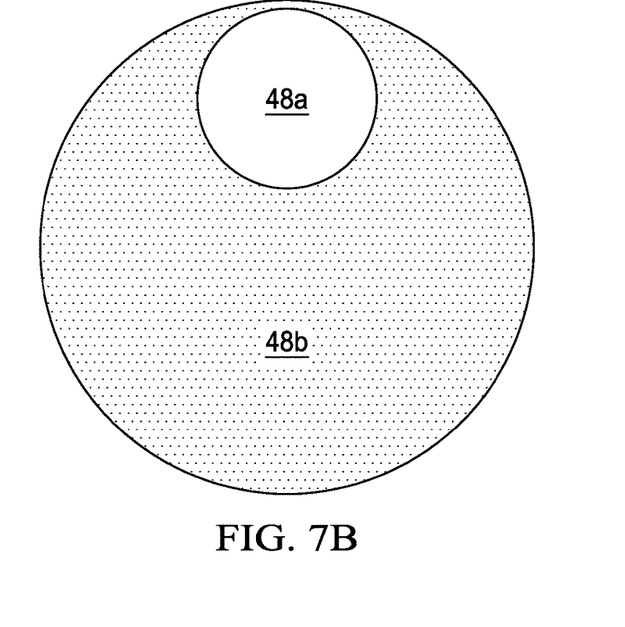

FIGS. 7A and 7B illustrate an example where the distal end of visualization fiber 32a has an angled surface 49a and the distal end of illumination fiber 32b has an angled surface 49b. Angled surface 49a has an angle F relative to probe axis 42, and angled surface 49b has an angle E relative to probe axis 42. Angles E and F may be any angles suitable to yield light 40a and 40b with axes 44a and 44b that results in the desired offset angle D. For example, angles E and F be in a range of 10 to 25, 25 to 50, or 50 to 75 degrees, and they may be the same or different angles.

A component (e.g., a computer) of the systems and apparatuses disclosed herein may include an interface, logic, and/or memory, any of which may include hardware and/or software. An interface can receive input to the component, provide output from the component, and/or process the input and/or output. Logic can perform the operations of the component, e.g., execute instructions to generate output from input. Logic may be a processor, such as one or more computers or one or more microprocessors. Logic may be computer-executable instructions encoded in memory that can be executed by a computer, such as a computer program or software. A memory can store information and may comprise one or more tangible, non-transitory, computer-readable, computer-executable storage media. Examples of memory include computer memory (e.g., Random Access Memory (RAM) or Read Only Memory (ROM)), mass storage media (e.g., a hard disk), removable storage media (e.g., a Compact Disk (CD) or a Digital Video Disk (DVD)), and network storage (e.g., a server or database).

Although this disclosure has been described in terms of certain embodiments, modifications (such as substitutions, additions, alterations, or omissions) of the embodiments will be apparent to those skilled in the art. Accordingly, modifications may be made to the embodiments without departing from the scope of the invention. For example, modifications may be made to the systems and apparatuses disclosed herein. The components of the systems and apparatuses may be integrated or separated, and the operations of the systems and apparatuses may be performed by more, fewer, or other components. As another example, modifications may be made to the methods disclosed herein. The methods may include more, fewer, or other steps, and the steps may be performed in any suitable order.

What is claimed is:

1. An illuminating endoprobe system comprising:
   one or more light sources configured to generate a visualization light and an illumination light;
   a housing configured to receive the visualization light and the illumination light, the housing comprising a probe tip with a probe axis, wherein the probe tip comprises a distal most open face on the housing;
   a vitreous visualization fiber disposed within the probe tip and having a distal end, the vitreous visualization fiber configured to transmit the visualization light through the probe tip, the visualization light having a visualization axis and a visualization beam angle at the probe tip; and
   a general illumination fiber disposed within the probe tip and having a distal end, the general illumination fiber configured to transmit the illumination light through the probe tip, the illumination light having an illumination axis and an illumination beam angle at the probe tip, the illumination beam angle greater than the visualization beam angle, the illumination axis at an offset angle relative to the visualization axis, the offset angle greater than 5 degrees;
   wherein the visualization light is projected out of a distal-most face of the visualization fiber and toward the distal most open face of the probe tip; and
   wherein the illumination light is projected out of a distal-most face of the general illumination fiber and toward the distal most open face of the probe tip.

2. The illuminating endoprobe system of claim 1, the distal end of the vitreous visualization fiber ramped relative to the probe axis, the ramped distal end transmitting the visualization light with the visualization axis that is not parallel to the probe axis.

3. The illuminating endoprobe system of claim 1, the distal end of the vitreous visualization fiber having an angled surface, the angled surface transmitting the visualization light with the visualization axis that is not parallel to the probe axis to yield the offset angle with the illumination axis.

4. The illuminating endoprobe system of claim 1, the distal end of the general illumination fiber having an angled surface, the angled surface transmitting the illumination light with the illumination axis that is not parallel to the probe axis to yield the offset angle with the visualization axis.

5. The illuminating endoprobe system of claim 1:
   the distal end of the vitreous visualization fiber having a first angled surface that transmits the visualization light with the visualization axis; and
   the distal end of the general illumination fiber having a second angled surface that transmits the illumination light with the illumination axis, the illumination axis and the visualization axis yielding the offset angle.

6. The illuminating endoprobe system of claim 1, the one or more light sources comprising:
   a visualization source configured to generate the visualization light; and
   an illumination source configured to generate the illumination light.

7. The illuminating endoprobe system of claim 1, the one or more light sources comprising:
   a visualization source configured to generate the visualization light; and
   an illumination source configured to generate the illumination light, a luminous flux of the visualization source greater than a luminous flux of the illumination source.

8. The illuminating endoprobe system of claim 1, the offset angle less than 30 degrees.

9. The illuminating endoprobe system of claim 1, the visualization light and the illumination light yielding non-concentric illumination patterns.

10. The illuminating endoprobe system of claim 1, wherein the vitreous visualization fiber is a different fiber than the general illumination fiber.

11. The illuminating endoprobe system of claim 10, wherein the vitreous visualization fiber only projects visualization light and wherein the general illumination fiber only projects illumination light.

12. A method for providing illumination and visualization, comprising:
- generating a visualization light and an illumination light;
- receiving the visualization light and the illumination light at a housing, the housing comprising a probe tip with a probe axis, wherein the probe tip comprises a distal most open face on the housing;
- transmitting the visualization light via a vitreous visualization fiber through the probe tip, the vitreous visualization fiber disposed within the probe tip and having a distal end, the visualization light having a visualization axis and a visualization beam angle at the probe tip, wherein the visualization light is projected out of a distal-most face of the visualization fiber and toward the distal most open face of the probe tip; and
- transmitting the illumination light via a general illumination fiber through the probe tip, the general illumination fiber disposed within the probe tip and having a distal end, the illumination light having an illumination axis and an illumination beam angle at the probe tip, the illumination beam angle greater than the visualization beam angle, the illumination axis at an offset angle relative to the visualization axis, the offset angle greater than 5 degrees,
- wherein the illumination light is projected out of a distal-most face of the general illumination fiber and toward the distal most open face of the probe tip.

13. The method of claim 12, the distal end of the vitreous visualization fiber ramped relative to the probe axis, the ramped distal end transmitting the visualization light with the visualization axis that is not parallel to the probe axis.

14. The method of claim 12, the distal end of the vitreous visualization fiber having an angled surface, the angled surface transmitting the visualization light with the visualization axis that is not parallel to the probe axis to yield the offset angle with the illumination axis.

15. The method of claim 12, the distal end of the general illumination fiber having an angled surface, the angled surface transmitting the illumination light with the illumination axis that is not parallel to the probe axis to yield the offset angle with the visualization axis.

16. The method of claim 12:
- the distal end of the vitreous visualization fiber having a first angled surface that transmits the visualization light with the visualization axis; and
- the distal end of the general illumination fiber having a second angled surface that transmits the illumination light with the illumination axis, the illumination axis and the visualization axis yielding the offset angle.

17. The method of claim 12, wherein the vitreous visualization fiber is a different fiber than the general illumination fiber.

18. The method of claim 17, wherein the vitreous visualization fiber only projects visualization light and wherein the general illumination fiber only projects illumination light.

* * * * *